US00RE39995E

(19) United States
(12) Reissued Patent
Pepper et al.

(10) Patent Number: US RE39,995 E
(45) Date of Reissued Patent: Jan. 1, 2008

(54) MINIMALLY INVASIVE INTRAMEDULLARY NAIL INSERTION INSTRUMENTS AND METHOD

(75) Inventors: John Pepper, Cheshire, CT (US); Thomas A. Russell, Eads, TN (US); Roy Sanders, Tampa, FL (US); Christopher E. Johnson, Germantown, TN (US)

(73) Assignee: Smith & Nephew, Inc., Memphis, TN (US)

(21) Appl. No.: 09/951,983

(22) Filed: Sep. 13, 2001

Related U.S. Patent Documents

Reissue of:
(64) Patent No.: 5,951,561
Issued: Sep. 14, 1999
Appl. No.: 09/107,644
Filed: Jun. 30, 1998

(51) Int. Cl.
*A61B 17/00* (2006.01)
A61F 5/00

(52) U.S. Cl. ..... 606/80; 606/79; 606/86

(58) Field of Classification Search ..... 606/80, 606/79, 81, 84, 85, 86, 87, 62
See application file for complete search history.

(56) References Cited

U.S. PATENT DOCUMENTS

| | | | | | |
|---|---|---|---|---|---|
| 4,466,429 | A | | 8/1984 | Loscher et al. | |
| 4,927,424 | A | * | 5/1990 | McConnell et al. | 606/96 |
| 5,443,469 | A | * | 8/1995 | Smith | 606/86 |
| 5,489,284 | A | * | 2/1996 | James et al. | 606/62 |
| 5,507,801 | A | * | 4/1996 | Gisin et al. | 606/86 |
| 5,569,262 | A | * | 10/1996 | Carney | |
| 5,569,269 | A | * | 10/1996 | Hart et al. | 606/144 |
| 5,601,550 | A | * | 2/1997 | Esser | 606/54 |
| 5,624,447 | A | * | 4/1997 | Myers | 606/96 |
| 5,632,759 | A | | 5/1997 | Rexroth | |
| 5,645,545 | A | * | 7/1997 | Bryant | 606/62 |
| 5,667,509 | A | * | 9/1997 | Westin | 606/80 |
| 5,725,532 | A | * | 3/1998 | Shoemaker | 623/1.11 |
| 5,814,049 | A | * | 9/1998 | Pratt et al. | 606/80 |

OTHER PUBLICATIONS

Smith & Nephew The Smith & Nephew Femoral Interlocking Nails—Surgical Technique—(Three pages).*
Craig B. Ordway, AIM Titanium Femoral Nail System—Sales Support Guide (Five Pages) M.D., New York.*

* cited by examiner

*Primary Examiner*—Pedro Philogene
(74) *Attorney, Agent, or Firm*—Kilpatrick Stockton LLP

(57) ABSTRACT

A minimally invasive reaming assembly for creating an entry portal into the canal of a bone and for providing a working channel in which to ream the canal of a bone. The assembly includes a sleeve, a housing and an inner reamer. The sleeve is an elongated cylindrically-shaped hollow sleeve that has a proximal and a distal end, with the distal end having a plurality of cutting blades. The housing is attached to the sleeve and is generally cylindrical in shape and it has a top portion, a bottom portion and a through bore. The top portion includes a releasable locking mechanism for engaging the inner reamer within the housing. The inner reamer has an elongated cannulated body and proximal and distal ends. The distal end has a rotatable reaming head and the proximal end has a drill shaft and a connector for connection to a drill. A portion of the body includes an annular collar with a tab for engaging a notch in the housing. The reamer is sized and shaped for insertion through the bore of the housing and the sleeve. The reaming assembly is configured to create an entry portal into the canal of a bone and to provide a working channel in which a plurality of reamers of graduated sizes are inserted for progressively reaming the canal of a bone.

51 Claims, 13 Drawing Sheets

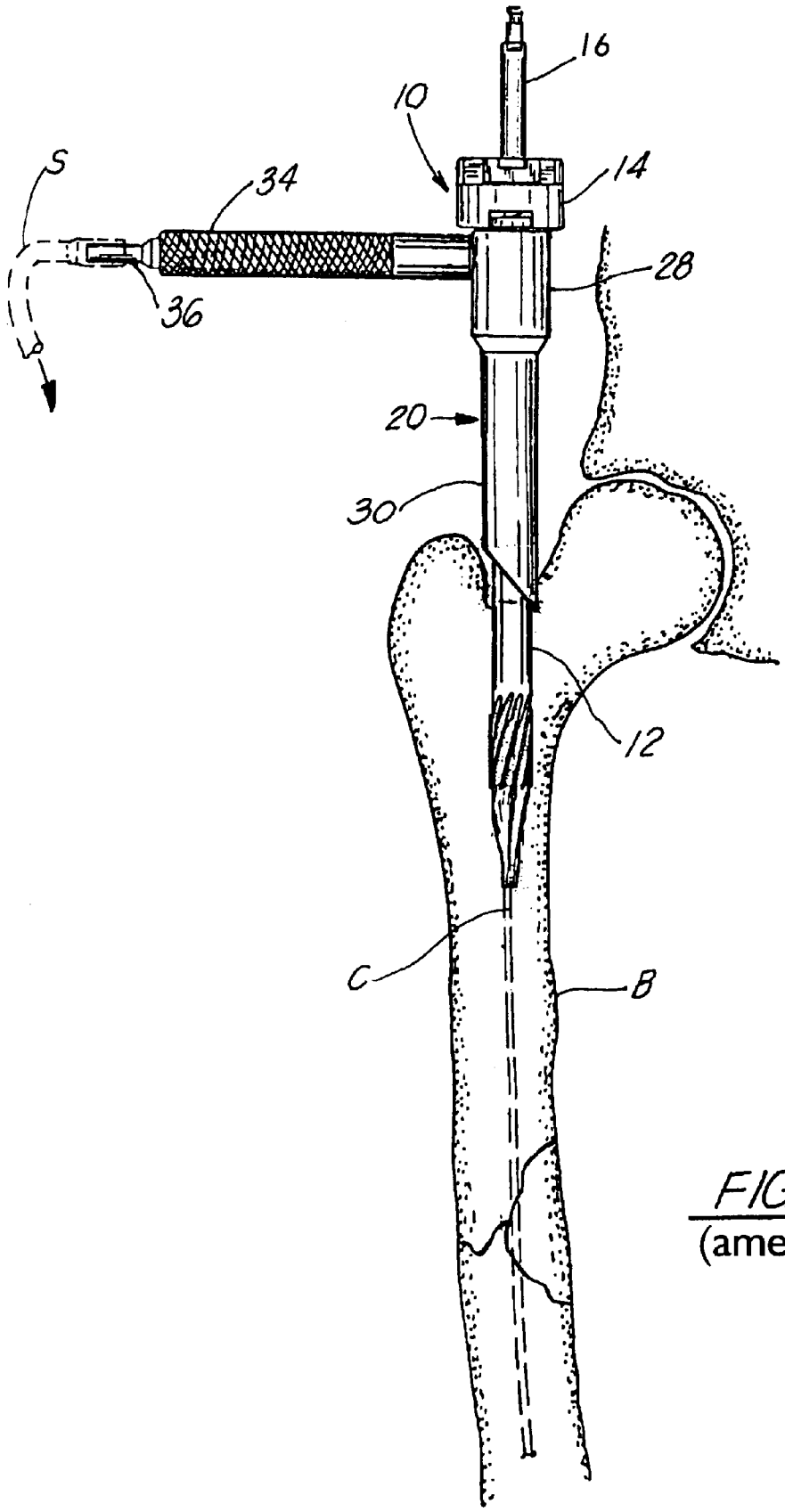
FIG. 1
(amended)

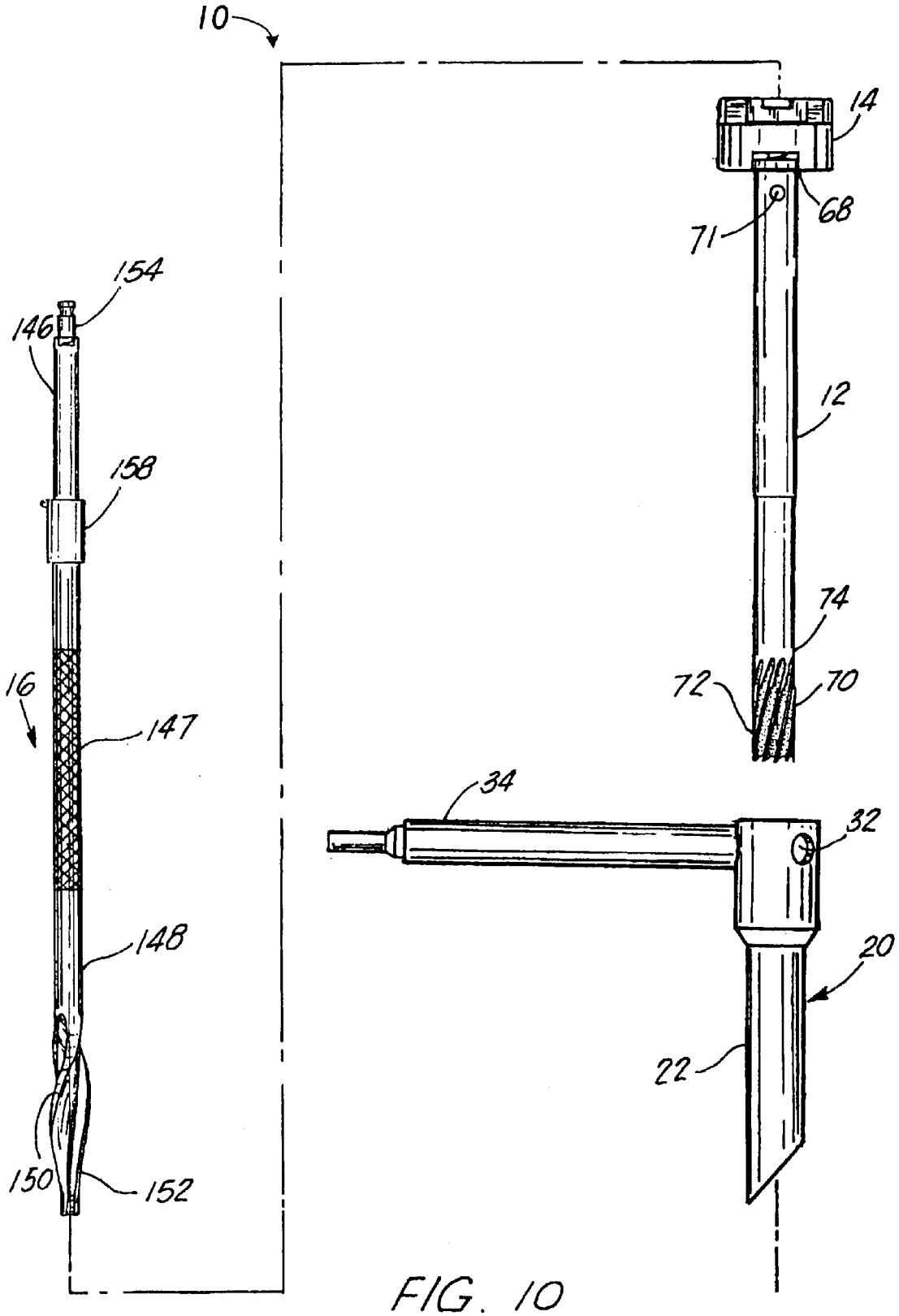
FIG. 10
(amended)

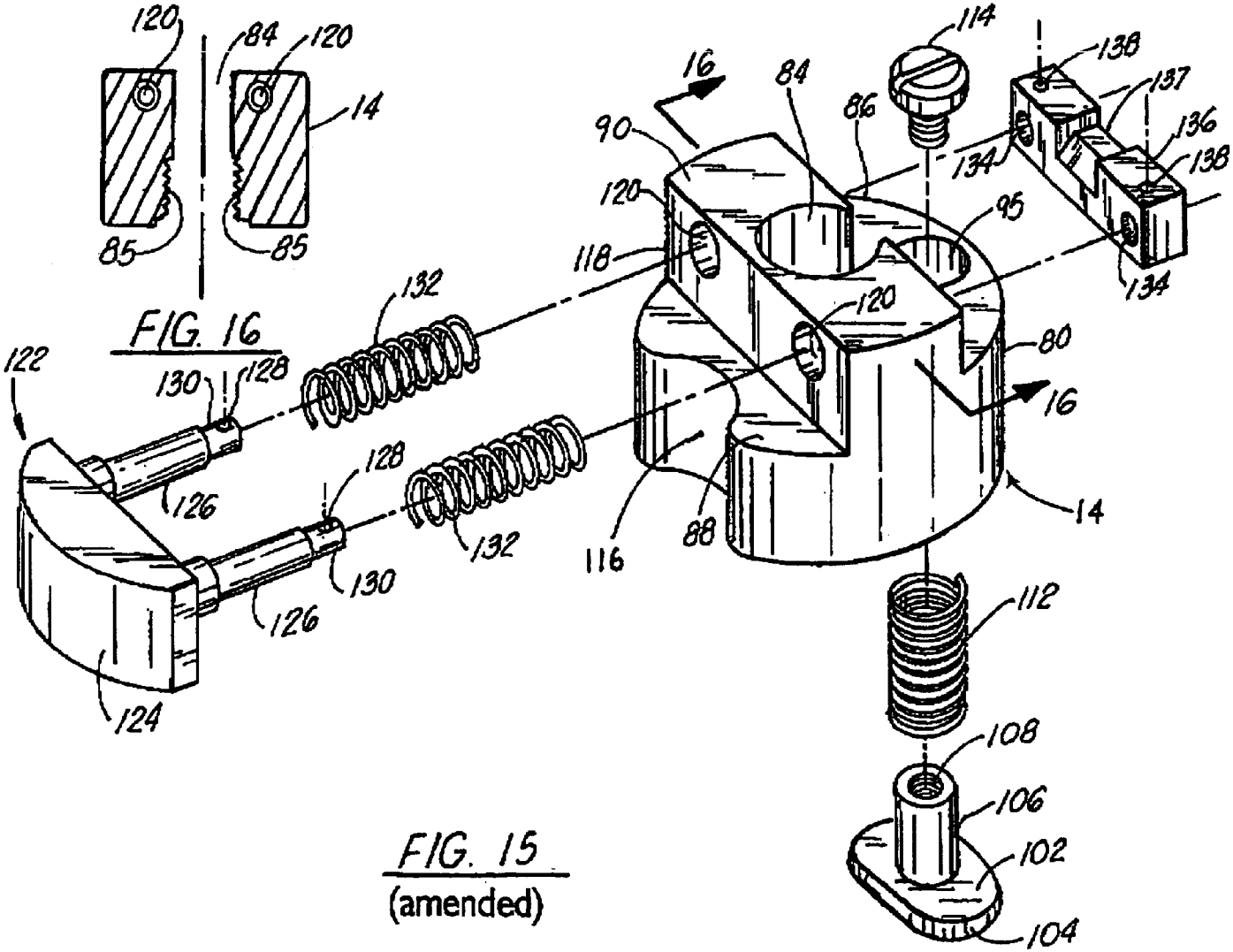
FIG. 15
(amended)
FIG. 16

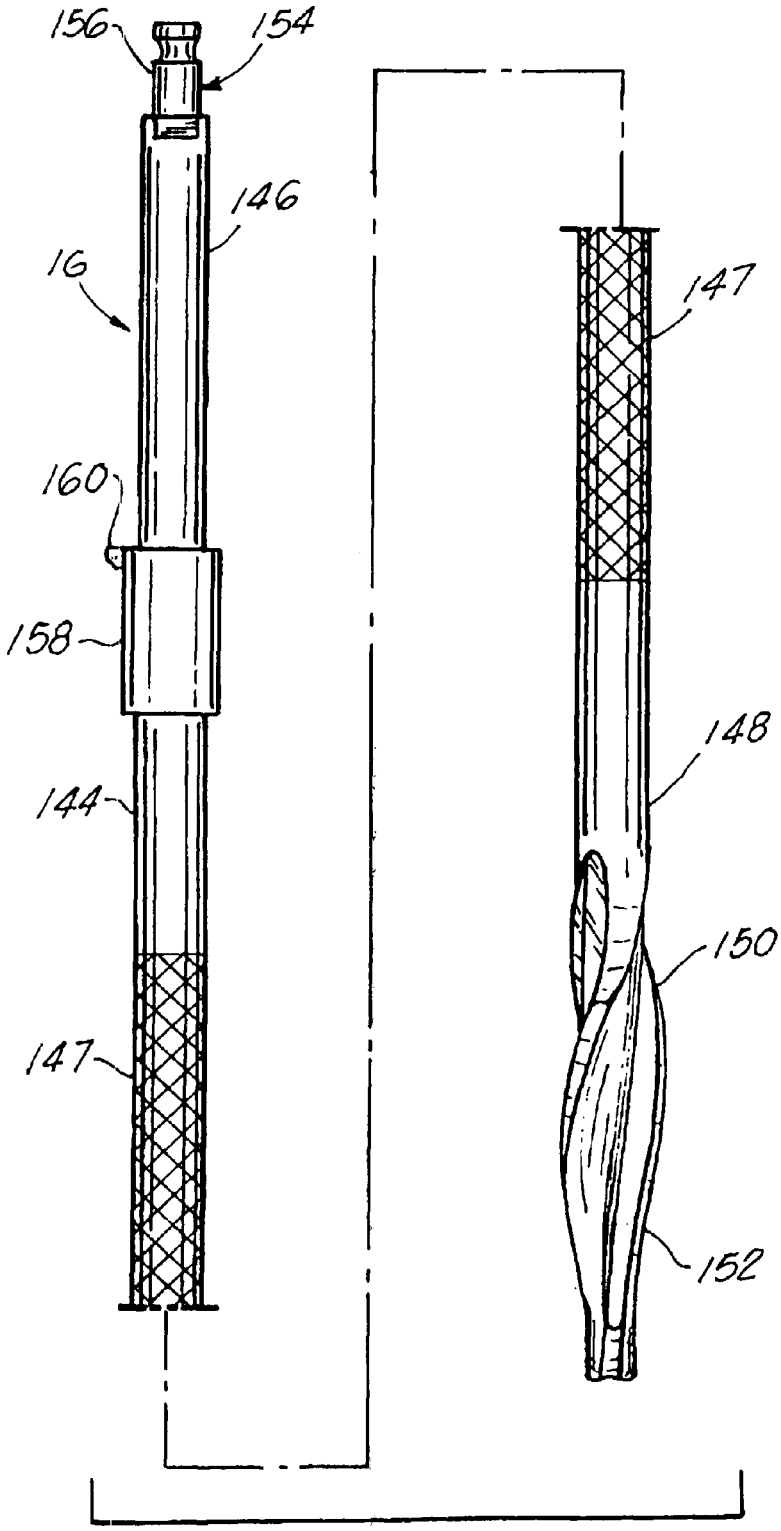
FIG. 22
FIG. 23
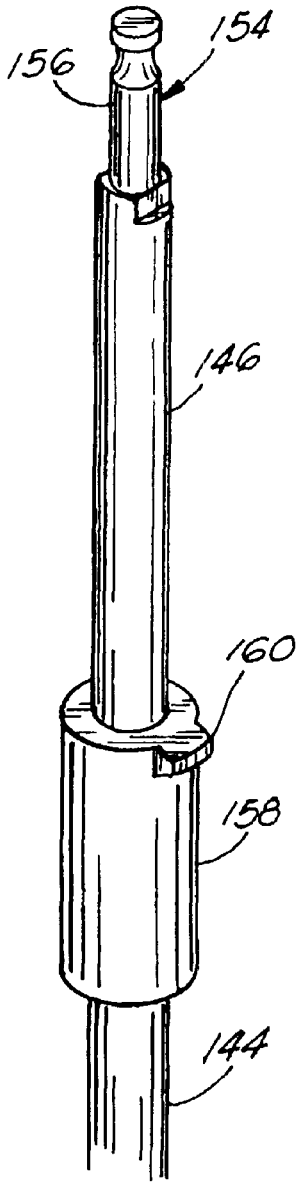

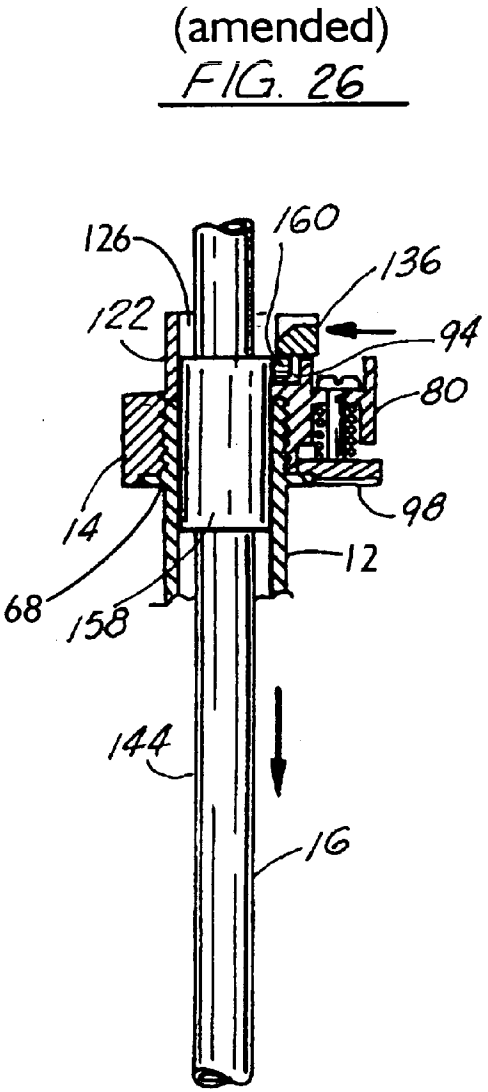
(amended)
FIG. 26
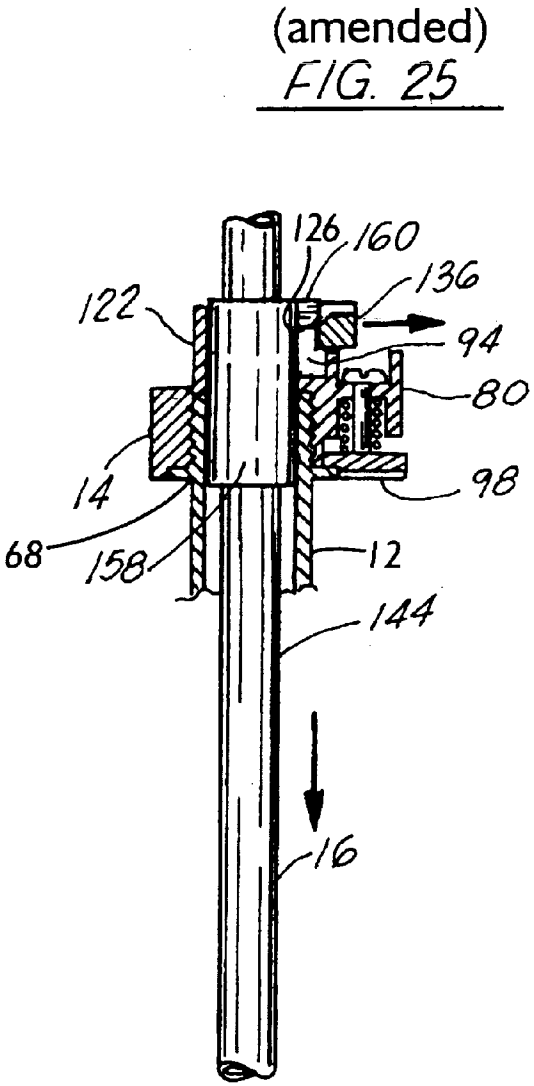
(amended)
FIG. 25
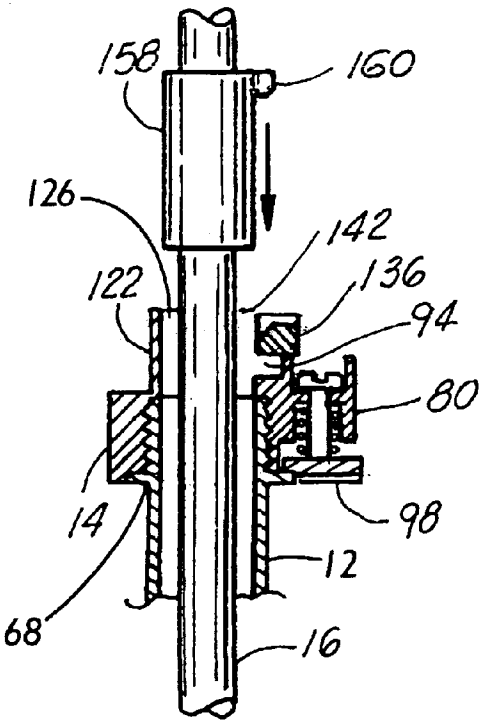
FIG. 24
(amended)

MINIMALLY INVASIVE INTRAMEDULLARY NAIL INSERTION INSTRUMENTS AND METHOD

Matter enclosed in heavy brackets [ ] appears in the original patent but forms no part of this reissue specification; matter printed in italics indicates the additions made by reissue.

FIELD OF THE INVENTION

The present invention relates to a surgical tool and method for accessing the intramedullary canal of a bone and more particularly to a minimally invasive reaming assembly and method for creating an entry portal into the canal of a bone and providing a working channel for reaming the canal of the bone to receive an intramedullary fracture reduction device.

BACKGROUND OF THE INVENTION

Bone fractures are repaired by inserting bone fracture reduction rods or intramedullary nails into the intramedullary canal of a bone in order to stay the fracture. In performing this type of surgery for femoral fractures for example, it is conventional to make an incision near the tip of the greater trochanter extending proximally in line with the fibers of the gluteus in order to create an entry portal through the bone and into the canal. However, it has been found to be difficult to correctly position the entry portal to the intramedullary canal from the greater trochanter and to ream the canal to the desired size without damaging the surrounding soft tissue, displacing the previously reduced fracture, or making extremely large incisions. This is especially true if the patient is obese or if flexion or abduction of the proximal fragment causes a portion of the greater trochanter to lie against the ilium.

In this type of surgery, after the entry portal has been established, the canal is progressively reamed to a larger diameter from a smaller diameter in increments of about 0.5 mm, from generally about 8 mm, up to generally about 12.5 mm. Typically, the surgeon starts with a small reamer, reams the bone, removes the reamer and then inserts a second reamer, 0.5 mm larger in diameter than the previous reamer. The surgeon repeats this process until he has reached the required canal diameter for the intramedullary nail that has been selected for the patient.

Additionally, this type of surgery can be particularly bloody which presents other problems. Excess blood can obstruct the surgeon's view of the site being reamed and excessive blood flowing from the surgical site can create problems for the surgical staff particularly if the patient has a blood or bone disease. Thus, it is important that the surgical instrumentation provide for suctioning of the blood created by the surgery from the surgical site.

Several other problems are encountered during the process of repeatedly inserting the different sized reamers in and out of the bone. First, the surgeon can lose the entry portal, even though there may be a guide rod in place, as the soft tissues close around the slender guide rod, eliminating from view the entry portal opening. Further, as the reamers are slid over the guide rod and into the soft tissues, the sharp edges of each reamer rub against the soft tissues. Because this process is repeated a number of times during the reaming process, the soft tissues become very irritated and torn. Additionally, the guide rod can be pulled out of the bone when a reamer is being withdrawn.

A second problem has to do with the actual entry of the reamer into the intramedullary canal of the bone after it has passed through the soft tissues. Since the guide rod is so much smaller than the reamer (3 mm compared to at least 8 mm), the guide rod frequently will not stay centered in the opening created by the previous reamer, which results in the next reamer getting caught on the edge of the opening created by the previous reamer. Since the next reamer is larger in size, it will not fit smoothly into the opening created by the previous smaller reamer. This situation prevents the surgeon from being able to determine if the next larger reamer is correctly centered before he or she starts reaming the canal. In order for the surgeon to locate the opening with the present instrumentation, he typically has to make a larger incision in order to locate the entry portal and determine the correct centering of the reamers.

There have been a number of attempts to solve these problems. One attempt is found in U.S. Pat. No. 5,624,447 which describes a surgical tool guide and entry portal positioner that provides a cannulated sleeve with a handle and a C-shaped soft tissue protector secured to the sleeve. U.S. Pat. No. 5,569,262 describes a guide tool for surgical devices that is used for directing a surgical device into attachment with a bone segment and is used to protect a surgeon's fingers from the surgical device and from the jagged surface of the bone segment. U.S. Pat. No. 5,443,469 describes a tubular tissue protection guard that is inserted into an incision or wound in order to accommodate reaming devices.

While these devices provide protection to the soft tissues, none of them provide a working channel within the bone canal in which to progressively ream out the intramedullary canal of the bone. It would be advantageous to have a device that can be used to both open the entry portal into the canal of a bone and to provide a working channel in which to ream the canal of the bone in a minimally invasive [mannor] *manner*. It also would be advantageous to be able to use the subject invention in combination with an entry portal tool that can be used to locate the most desirable placement of the entry portal into the bone.

SUMMARY OF THE INVENTION

The present invention consists of a minimally invasive reaming assembly and method for creating an entry portal into the canal of a bone and for providing a working channel in which to ream the canal of a bone. The assembly includes a sleeve, a housing and an inner reamer. The sleeve is an elongated cylindrically-shaped hollow sleeve that has a proximal and a distal end, with the distal end having a plurality of cutting blades. The housing is adjacent to the sleeve and has a top portion, a bottom portion and a through bore. The top portion includes a releasable locking mechanism for engaging the inner reamer within the housing.

The inner reamer has an elongated body and proximal and distal ends. The distal end has a rotatable reaming head and the proximal end has a drill shaft and connecting means for connection to a drill. A portion of the body includes an annular collar with a tab for engaging a notch in the housing. The inner reamer is sized and shaped for insertion through the bore of the housing and the sleeve. The reaming assembly allows for the passage of reamers of graduated sizes for progressively reaming the canal of a bone through the sleeve. In a preferred embodiment, the reaming assembly is used in combination with an entry portal tool for use in correctly placing the entry portal in the bone

BRIEF DESCRIPTION OF THE DRAWINGS

A better understanding of the invention can be obtained when the detailed description of exemplary embodiments set forth below is reviewed in conjunction with the accompanying drawings, in which:

FIG. 1 is a schematic view of the present invention being used to ream the intramedullary canal of a bone;

FIG. 10 is an exploded view of the assembly of FIG. 8;

FIG. 15 is an exploded perspective view of the housing of the present invention;

FIG. 16 is a cross-sectional view of the housing of FIG. 15 taken along lines 16—16 of FIG. 15;

FIG. 22 is an exploded side plan view of the reaming component of the present invention of FIG. 8;

FIG. 23 is an enlarged view of a portion of the reaming component of FIG. 22; and FIGS. 24–26 are partial cross-sectional views of the connecting mechanism between the inner reamer and the housing of FIG. 8.

DETAILED DESCRIPTION OF THE PREFERRED EMBODIMENT

Figure 2:
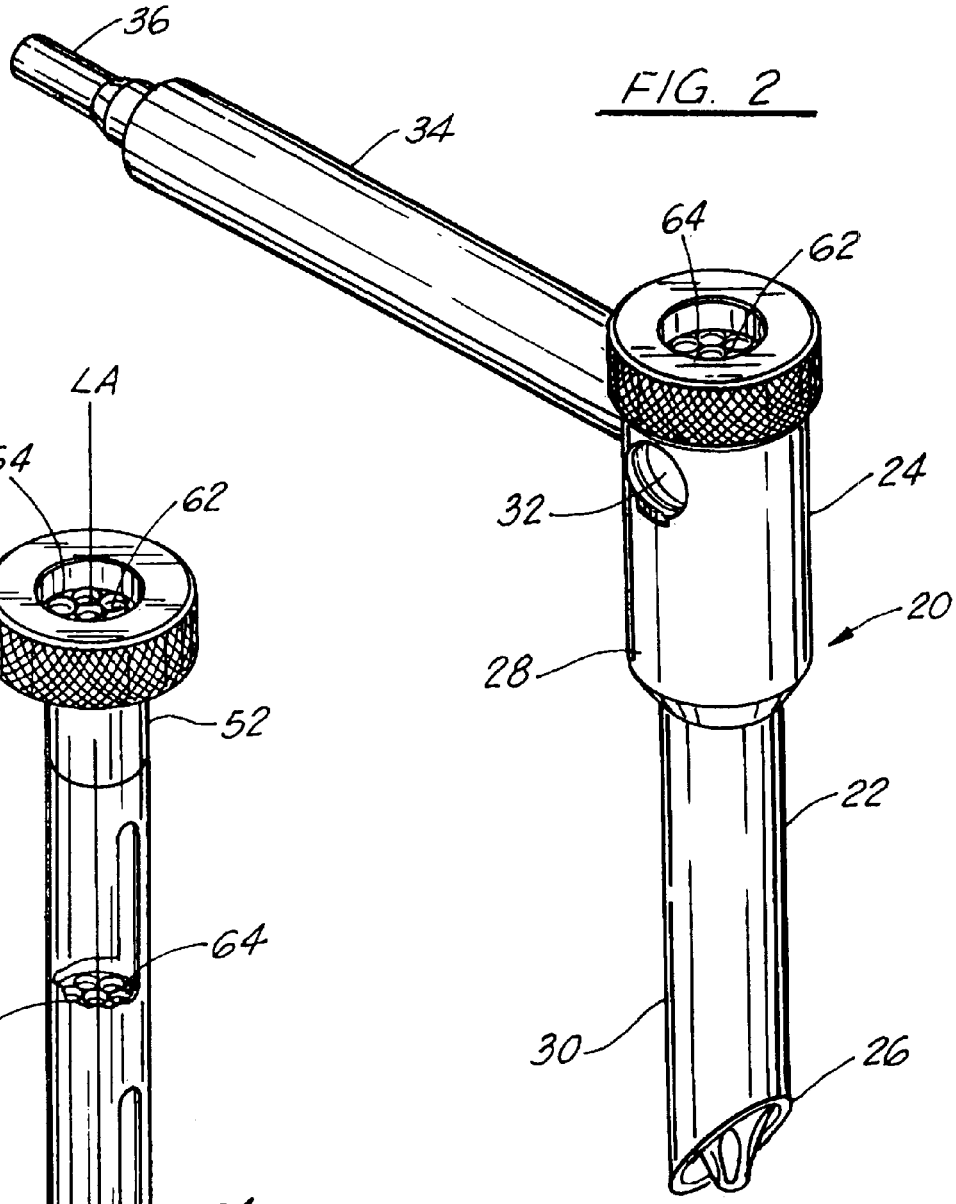
FIG. 2 is a prospective view of an entry portal tool used in combination with the present invention.

The present invention, as shown in FIGS. 1 and 10, is a minimally invasive reaming assembly 10 that includes a reaming sleeve 12, a housing 14 and an inner reamer 16 that fits within the cannulation of reaming sleeve 12. The reaming assembly 10 is used in combination with an entry portal tool 20 to locate the preferred placement of an entry portal and then to create an entry portal to the canal C of a bone B (FIGS. 1 and 2). Once the entry portal has been created and the reaming sleeve 12 is positioned in the bone B, the inner reamer 16 is removed from the housing 14 and reaming sleeve 12. The reaming sleeve 12 is then used as a working channel in which to progressively ream the canal of the bone B without losing the entry portal or irritating the soft tissue surrounding the entry portal. In a preferred embodiment, the entry portal tool 20 and the reaming assembly 10 are formed of stainless steel.

Figure 5:
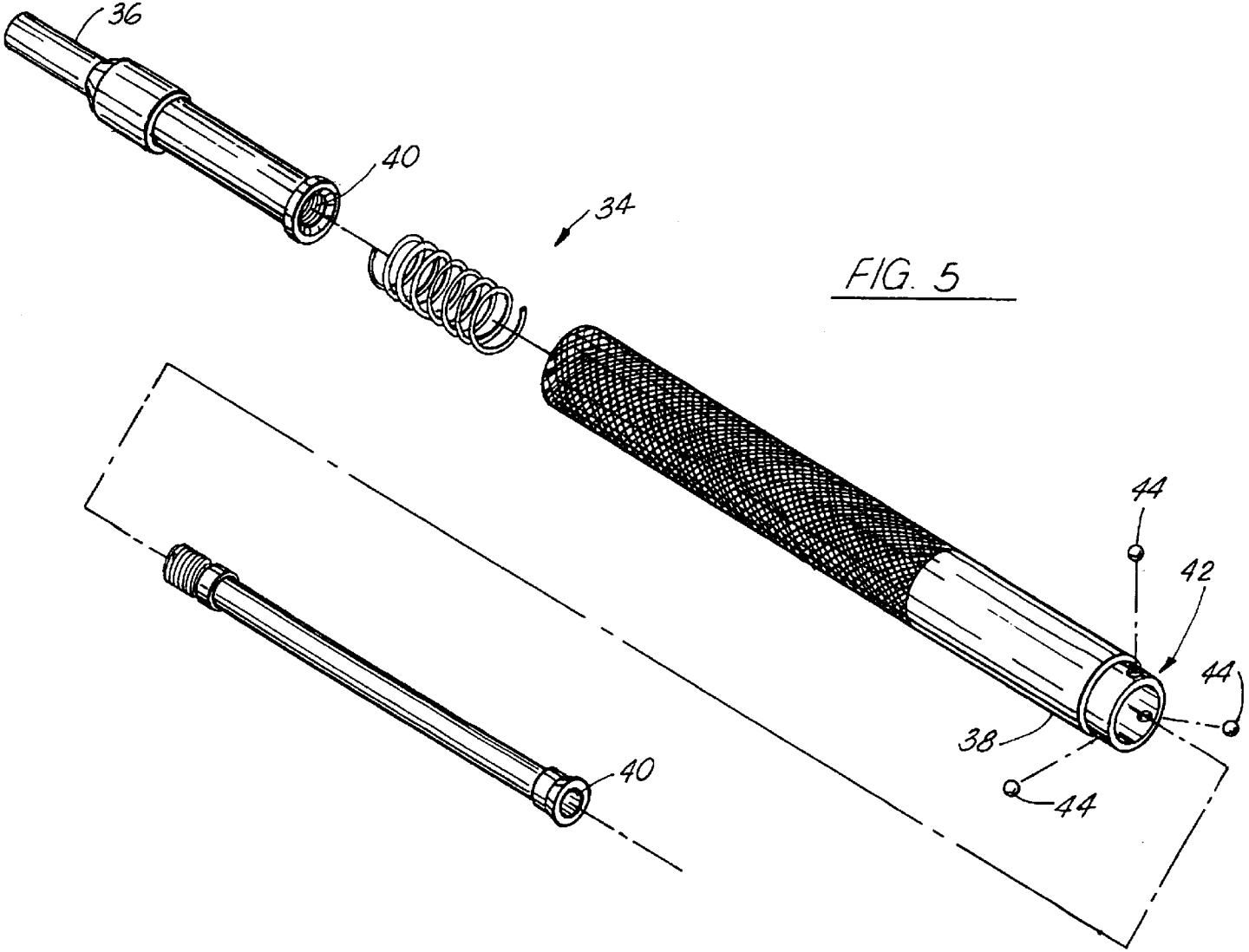
FIG. 5 is an exploded view of the handle of the entry portal tool of FIG. 2.

Entry portal tool 20 is an elongated, cylindrically-shaped hollow sheath 22 having a proximal end 24, a beveled distal end 26 and an upper and lower portion 28, 30 (FIG. 2). The upper portion 28 includes at least one generally circular opening 32 in the sheath 22, and in a preferred embodiment has three openings. In one embodiment the openings 32 of the sheath 22 can be threaded. As shown in FIGS. 2 and 5, the entry portal tool 20 also includes a handle 34 that can be used by the surgeon to manipulate the entry portal tool 20. The handle 34 is elongated in shape and has proximal and distal ends 36, 38. The distal end 38 is [removeably] *removably* connected to a selected circular opening 32 in the sheath 22. The handle 34 includes a through bore 40, a connecting mechanism 42 for connecting and disconnecting the handle 34 to the sheath 22 (FIG. 5). The proximal end 36 is sized and shaped to accept a suction device S known to one skilled in the art that can be attached to the proximal end 36 of the handle 34 in order to suction fluids and bone debris from the reaming site (FIG. 1).

Figures 6A, 6B, 6C:
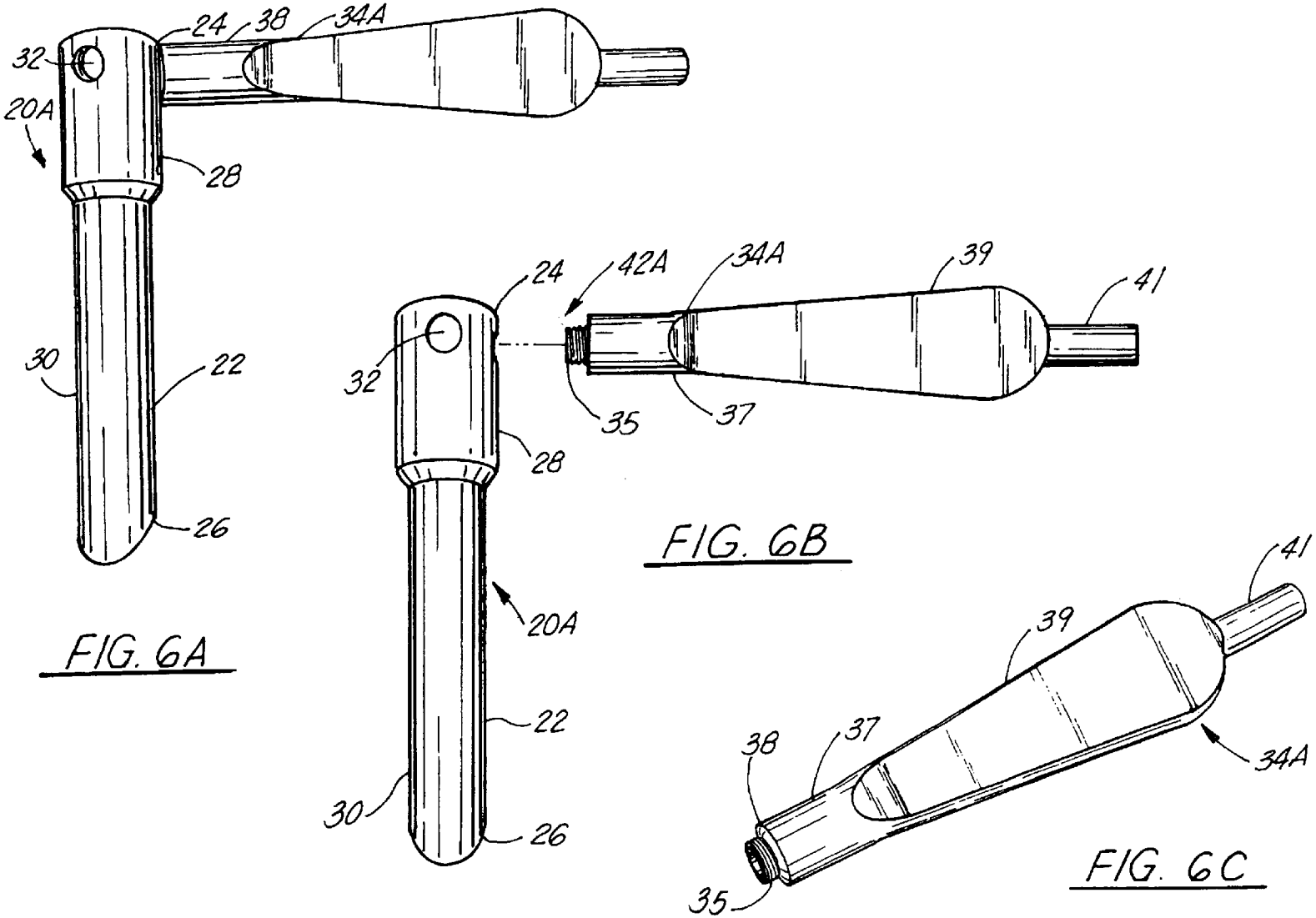
FIG. 6A is a side plan view of an alternate embodiment of an entry portal tool.
FIG. 6B is an exploded side plan view of the entry portal tool of FIG. 6A.
FIG. 6C is a prospective side view of the handle of the entry portal tool of FIG. 6B.

In one embodiment of the handle 34, as shown in FIG. 5, the connecting mechanism 42 is a spring-loaded plunger mechanism that utilizes a series of retractable ball bearings 44 to connect and disconnect the handle 34 from a selected circular opening 32 in the sheath 22. In a second embodiment of the entry portal tool 20A, as shown in FIGS. 6A-C, a handle 34A has a connecting mechanism 42A that is a threaded portion 35 at the distal end 38 of the handle 34A. The threaded portion 35 of the handle distal end 38 engages threading in the circular openings 32 of the sheath 22. Preferably, the handle 34A includes a generally cylindrical distal portion 37, a flat middle portion 39 and a generally cylindrical proximal end 41 that is configured to accept a suction device for suctioning fluids from the reaming site.

Figure 7A:
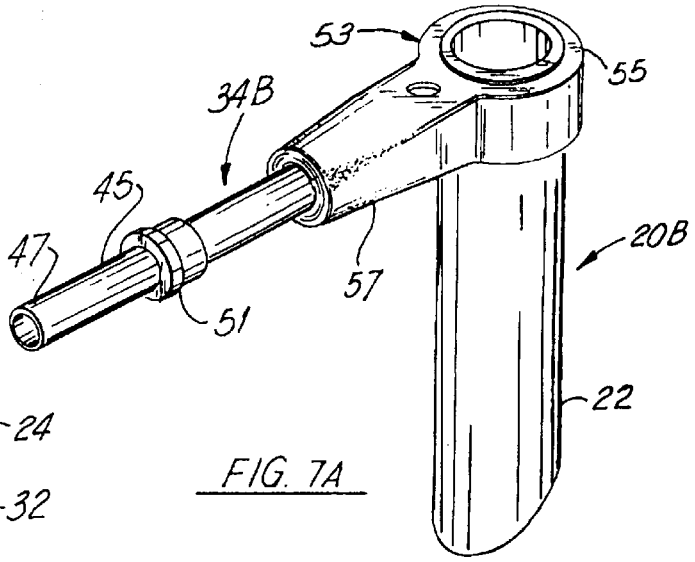
FIG. 7A is a prospective view of a third alternate embodiment of an entry portal tool.
Figure 7B:
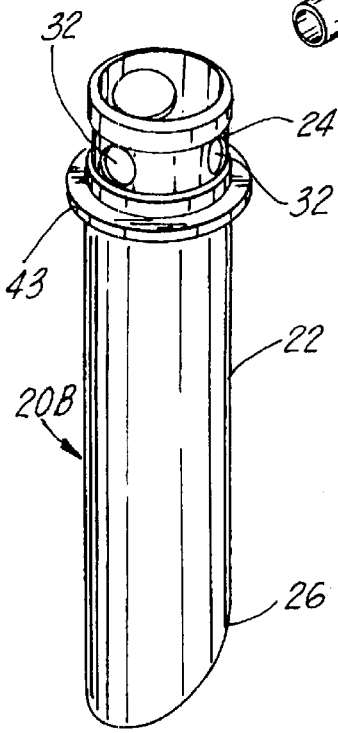
FIG. 7B is a side plan view of the sheath of the entry portal tool of FIG. 7A.
Figure 7D:
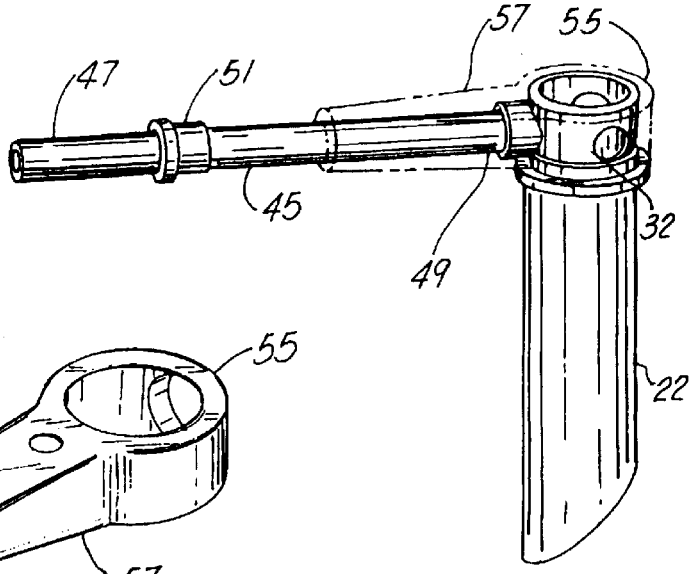
FIG. 7D is a side plan view of the entry portal tool of FIG. 7A with a portion of the handle in phantom.
Figure 7C:
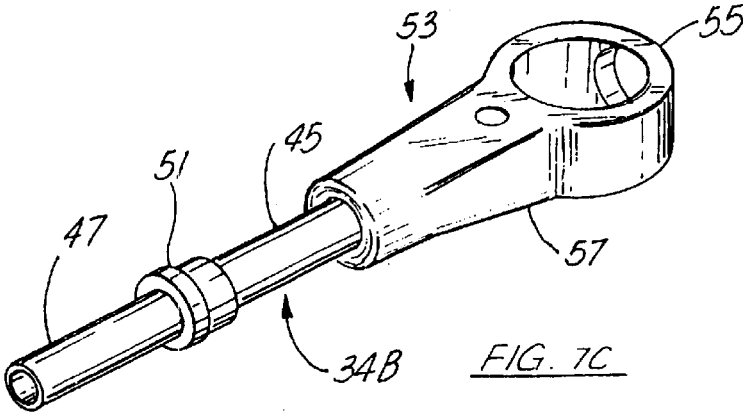
FIG. 7C is a prospective view of the handle of the entry portal tool of FIG. 7A.

A third embodiment of the entry portal tool 20B is shown in FIGS. 7A-C in which the proximal end 24 of the sheath 22 includes an annular lip 43 placed below circular openings 32. Handle 34B includes an elongated tubular member 45 having a proximal end 47, a distal end 49 and an annular collar 51 that serves as a gripper. Handle 34B also includes a connector portion 53 having a generally cylindrical ring 55 integral with an elongated housing 57. Housing 57 has a through bore 59 (*not shown*) sized and shaped to accommodate the distal end 49 of the tubular member 45. Ring 55 includes at least one generally circular opening 61 that is aligned with bore 59 and is similar in size and shape to the circular openings 32 of the handle 34B. Bore 59 and opening 61 (*not shown*) allow the distal end 49 of the tubular member 45 to be inserted into housing 57 with the distal end 49 extending into the interior of ring 55. Housing 57 includes a spring mechanism (not shown) connected to the tubular member 45, that allows the distal end 49 of the tubular member 45 to be retracted from the interior of the ring 55 so that ring 55 can be placed upon the proximal end 24 of sheath 22. The annular lip 43 provides a stop for connector portion 53. Once the housing 57 has been placed upon the sheath 22, with opening 32 and 61 being in alignment with each other, the tubular member 45 is released so that it extends through opening 32 a short distance into the interior of the ring 55 (FIG. 7D). The proximal end 47 of the tubular member 45 is configured to accept a suction device for suctioning fluids from the reaming site.

Figure 3:
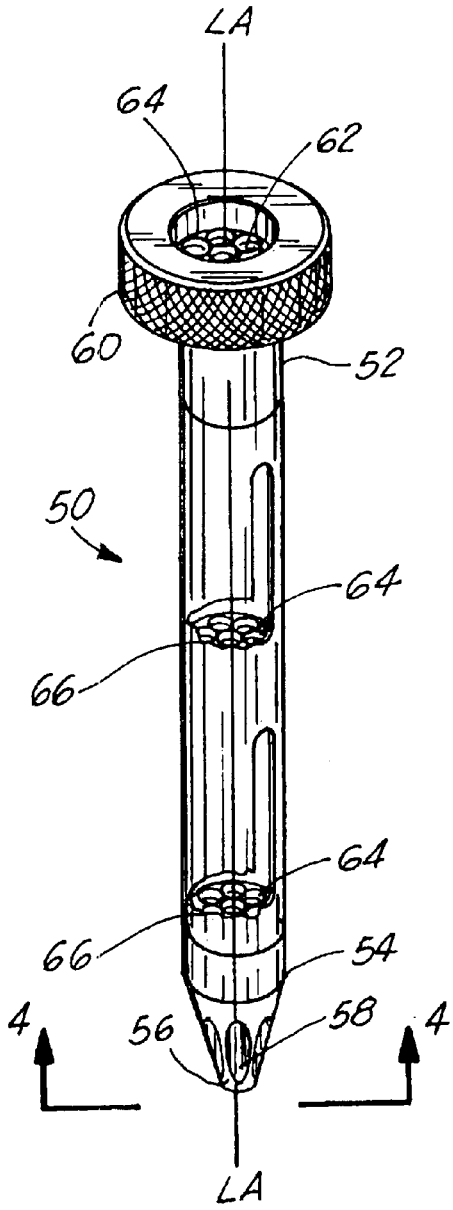
FIG. 3 is a prospective view of a cannulated obturator of the entry portal tool of FIG. 2.
Figure 4:
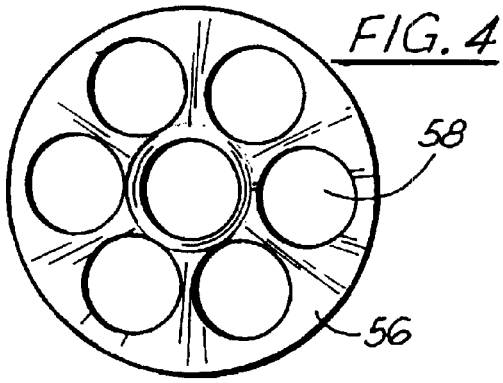
FIG. 4 is a bottom plan view of the obturator of FIG. 3 taken along lines 4—4.

Entry portal tools 20, 20A and B also include a cannulated obturator or elongated cylindrically-shaped tube 50 having a proximal and distal end 52, 54 and a central longitudinal axis LA (FIG. 3). The distal end 54 has a conical tip 56 that includes a plurality of openings 58. Preferably, the plurality of openings 58 have a circular center opening surrounded by five circular openings all of the same size, as shown in FIG. 4. The proximal end 52 includes an annular collar 60 having a diameter greater than tube 50 and sheath 22. Tube 50 includes a cylindrical hub 62 at its proximal end 52 with the hub 62 including a plurality of openings 64 identical in configuration to the openings 58 of the conical tip 56. Tube 50 also can include a number of cylindrical hubs 66, each having a plurality of openings 64, placed longitudinally in tube 50 between the proximal and distal ends 52, 54 of tube 50 (FIG. 3). The plurality of openings 64 of the hubs 62, 66, and the openings 58 of the conical tip 56 are aligned along parallel lines that are parallel with the central longitudinal axis LA of tube 50. Obturator 50 is sized and shaped for removably inserting into the hollow sheath 22 with the hollow sheath 22 being sized and shaped for removable insertion of the reaming sleeve 14 into the sheath 22 (FIG. 2).

Additionally, the entry portal tools 20, 20 A-B are configured to allow for the suctioning of blood out of the intramedullary canal into the reaming sleeve 12 and out the sheath 22 and through handle 34, 34A and B into a collection device.

As described above, the minimally invasive reaming assembly 10 includes reaming sleeve 12, housing 14 and inner reamer 16 (FIG. 10). Reaming sleeve 12, as shown in FIGS. 11–14, is an elongated cylindrically-shaped hollow sleeve having a proximal and distal end 68, 70. Distal end 70 includes a plurality of cutting blades 72 of the kind generally known by one skilled in the art of orthopaedic surgery for cutting into the canal of a bone. In a preferred embodiment, the cutting blades 72 extend approximate 35 mm up from the distal end 70 of sleeve 12 on the outer surface 74 of sleeve 12. The outer surface 74 of proximal end 68 of sleeve 12 includes threading 76 on approximately 6 mm in length of the proximal end 68. Positioned at the end of threading 76 is a ring of angled, horizontally extending teeth 78, in which the threading 76 and teeth 78 provide for engagement of the proximal end 68 of the sleeve 12 to the housing 14. Reaming sleeve 12 and housing 14 can be constructed as an integral unit, or sleeve 12 can be constructed without the housing 14 in which case the release mechanism for the inner reamer 16 would be part of the proximal end 68 of sleeve 12. In a preferred embodiment, the sleeve 12 and housing 14 are constructed of two separate pieces or elements that are connected together so that the reaming sleeve 12 can be replaced if necessary.

Figure 17:
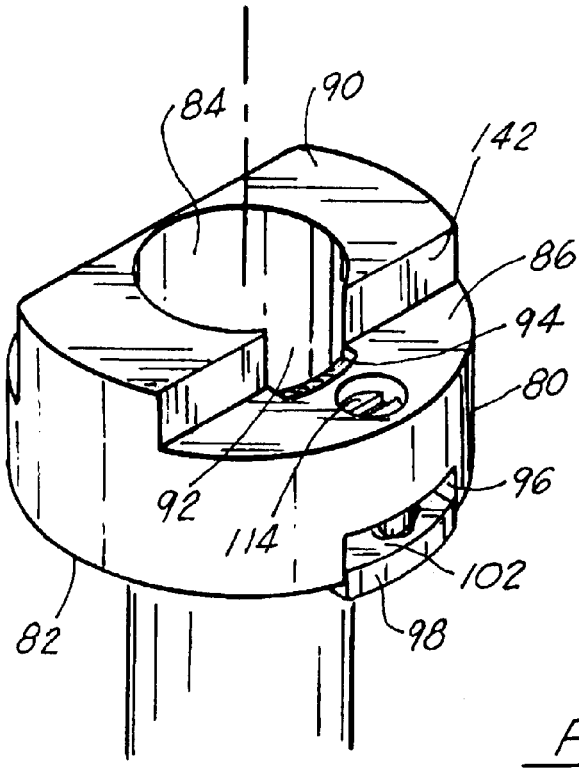
FIG. 17 is partial perspective view of the sleeve and housing of FIG. 9.
Figure 18:
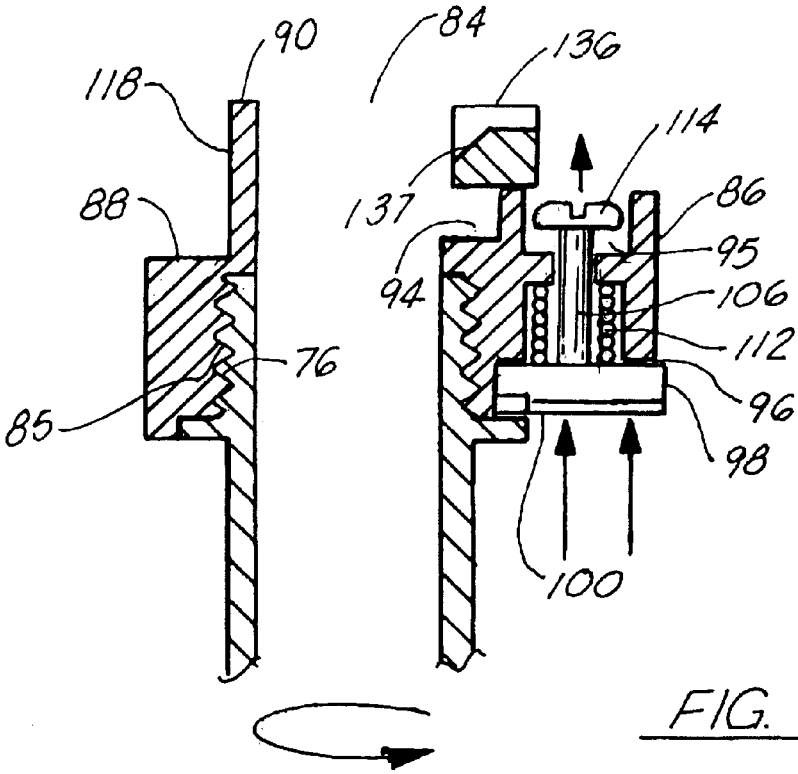
FIG. 18 is a partial cross-sectional view of the connection mechanism between the sleeve and the housing of FIG. 9.
Figure 19:
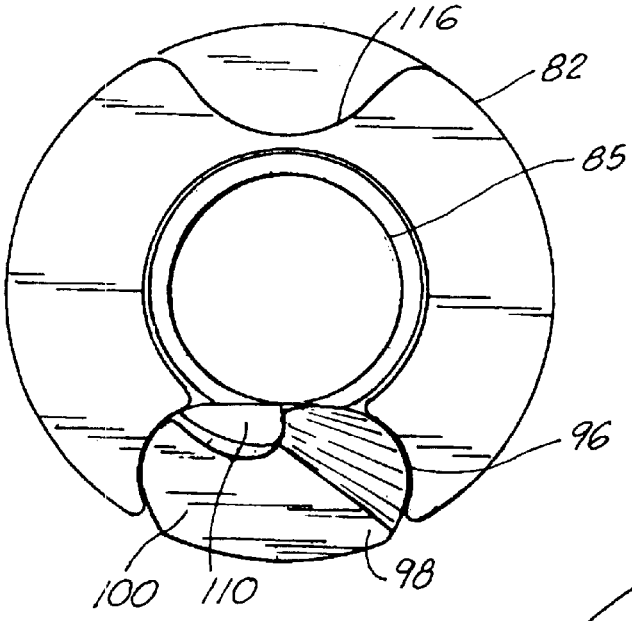
FIG. 19 is a plan view of the bottom of the housing of FIG. 15.
Figure 20:
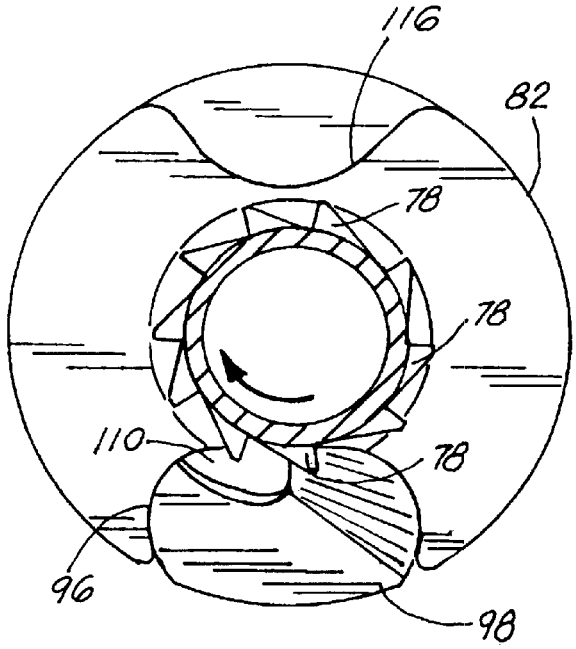
FIG. 20 is a plan view of the distal end of the sleeve showing the locking mechanism of the housing of FIG. 9 in an unlocked position.
Figure 21:
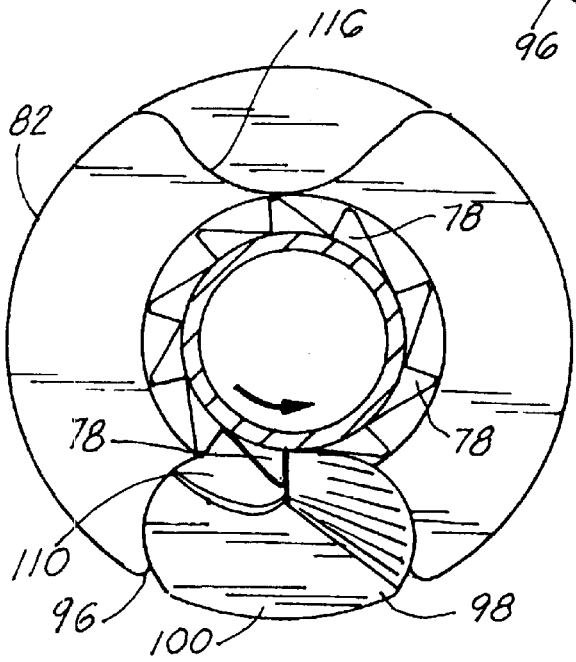
FIG. 21 is a plan view of the distal end of the sleeve showing the locking mechanism of the housing of FIG. 9 in a locked position.

As illustrated in FIGS. 15–18, housing 14 is preferably generally cylindrical in shape and includes a top portion 80, a bottom portion 82 and a centrally located, cylindrical through bore 84. Bore 84 includes threading 85 on a portion of the bore's 84 surface (FIGS. 16–18). The threading 85 on bore 84 is configured to mate with the threading 76 on the proximal end 68 of sleeve 12. Top portion 80 includes a first side 86 and a second side 88 separated by a raised center portion 90. First side 86 is approximately 6 mm lower than center portion 90, while second side 88 is approximately 10 mm lower than center portion 90 (FIG. 15). First side 86 intersects part of center portion 90 exposing a section of bore 84 creating opening 92 (FIGS. 17 and 18). Opening 92 is adjacent a notch 94 on the surface of the first side 86 of housing 14. Notch 94 is sized and shaped to engage a tab 160 on the inner reamer 16. First side 86 also includes a through bore 95 adjacent the notch 94 (FIGS. 15 and 17). As shown in FIGS. 16 and 20, the part of the bottom portion 82 that is in alignment with first side 86 includes a generally oval-shaped cutout 96, through which bore 95 passes. In a preferred embodiment, cutout 96 is shaped to accommodate a generally oval-shaped locking button 98. Locking button 98 has an outer side 100, an inner side 102, and side walls 104. The inner side 102 of button 98 includes an upwardly extending cylindrical shaft 106 having a threaded opening 108. A notch 110 is placed on a portion of the outer side 100 of button 98, with notch 110 being sized and shaped to catch one of the teeth 78 on sleeve 12 (FIGS. 19–21). Preferably, locking button 98 is a spring-loaded button that is attached to the housing by placing a spiral compression spring 112 over shaft 106 and inserting shaft 106 and spring 112 into bore 95. A threaded screw 114 is inserted into bore 95 from the first side 86 of housing 14 and engages the threaded opening 108 in shaft 106 (FIG. 15). Thus, as illustrated in FIGS. 24–26, a spring-loaded locking button 98 is provided that can be depressed in order to allow the proximal end 68 of sleeve 12 to be screwed into threaded portion 85 of bore 84 and then released, causing the notch 110 (*FIG. 21*) on button 98 to engage one of the teeth 78 on sleeve 12, locking sleeve 12 into the housing 14.

As shown in FIG. 15, a portion of the second side 88 of housing 14 includes a centrally located, generally semicircular cutout 116. Wall 118 of center portion 90 includes a pair of parallel, horizontally placed through bores 120 positioned on either side of bore 84 that are sized and shaped to accommodate the legs 126 of a release button 122. Release button 122 is provided in order to lock the reamer 16 or release the reamer 16 from housing 14 (FIGS. 24–26). In a preferred embodiment, as shown in FIG. 15, release button 122 is generally U-shaped in which base 124 of the U-shape is crescent-shaped and legs 126 of the U-shape are generally cylindrical. Each of legs 126 have a vertical opening 128 in their distal ends 130. Preferably, release button 122 is a spring-loaded button that is constructed by placing spiral compression springs 132 over legs 126 and inserting legs 126 and springs 132 through bores 120 in the center portion 90. The extending distal ends 130 of legs 126 are then inserted into corresponding openings 134 of a rectangular block 136, that includes a pair of vertical bores 138, that intersect the block openings 134. Pins (not shown) are inserted through vertical bores 138 and into openings 128 of legs 126 of the button 122, fastening the block 136 to the release button 122 (FIG. 15). In a preferred embodiment, the rectangular block 136 includes a beveled center section 137 that allows the inner reamer 16 to be locked in place without releasing button 122.

As illustrated in FIGS. 24–26, when the assembled release button 122 is in its closed position on the housing 14, block 136 is positioned against wall 142 of the center portion 90 which effectively covers notch 94 on the surface of the first side 86 of housing 14 (FIG. 24). When the spring-loaded release button 122 is pressed inwardly toward the center portion 90, block 136 moves away from wall 142 of the center portion 90, exposing notch 94 (FIG. 25).

The inner reamer 16 of the reaming assembly 10 has an elongated cannulated body 144 and proximal and distal ends 146, 148 (FIGS. 10 and 22). However, elongated body 144 can also formed from a solid rod that is not cannulated. Distal end 148 has a rotatable reaming head 150 of a type known to one skilled in the art of orthopaedic surgery (FIG. 22). The rotatable reaming head 150 includes a plurality of cutting blades 152 suitable for cutting through the intramedullary canal of a bone. The proximal end 146 of inner reamer 16 includes a connection mechanism 154 configured in the shape of a drive shaft 156 of a type known to one skilled in the art of orthopaedic surgery (FIG. 23). Any suitable connection mechanism 154 can be employed to interconnect or detachably connect the drive shaft 156 to a rotational driver, such as that found in a conventional reaming drill or other suitable device. In a preferred embodiment, inner reamer 16 can include a flexible center section 147 that allows the reamer 16 to also be used to ream the proximal tibia, thus eliminating the need for a separate instrument. The flexible center section 147 of inner reamer 16 can be formed by cutting concentric helical cuts in opposite directions in a metal tube so that torque can be applied. The concentric helical cuts will provide both rigidity and flexibility to the center section 147 of the inner reamer 16.

A portion of inner reamer 16 includes an annular collar 158 that is of a slightly larger diameter than the diameter of cannulated body 144 of inner reamer 16 (FIGS. 22 and 23). Collar 158 includes a tab 160 that is sized and shaped to mate with notch 94 of housing 14 in order to secure inner reamer 16 in the housing 14. As shown in FIGS. 24–26, inner reamer 16 is inserted into the housing 14 with the release button 122 in an open position which exposes notch 94 of housing 14. After tab 160 has been placed in notch 94, the button 122 is released, thus locking tab 160 in notch 94. Alternatively, the beveled center portion 137 of the block 136 allows tab 160 to slide into the notch 94 without having to expose notch 94.

In a preferred embodiment, a plurality of reamers (not shown) of graduated sizes are used with the reaming apparatus 10 for progressively reaming the canal of a bone after the initial reaming has been performed with the inner reamer 16. The reamers are typically graduated in 0.5 mm increments, however, other graduated dimensions are contemplated.

Figures 8, 9:
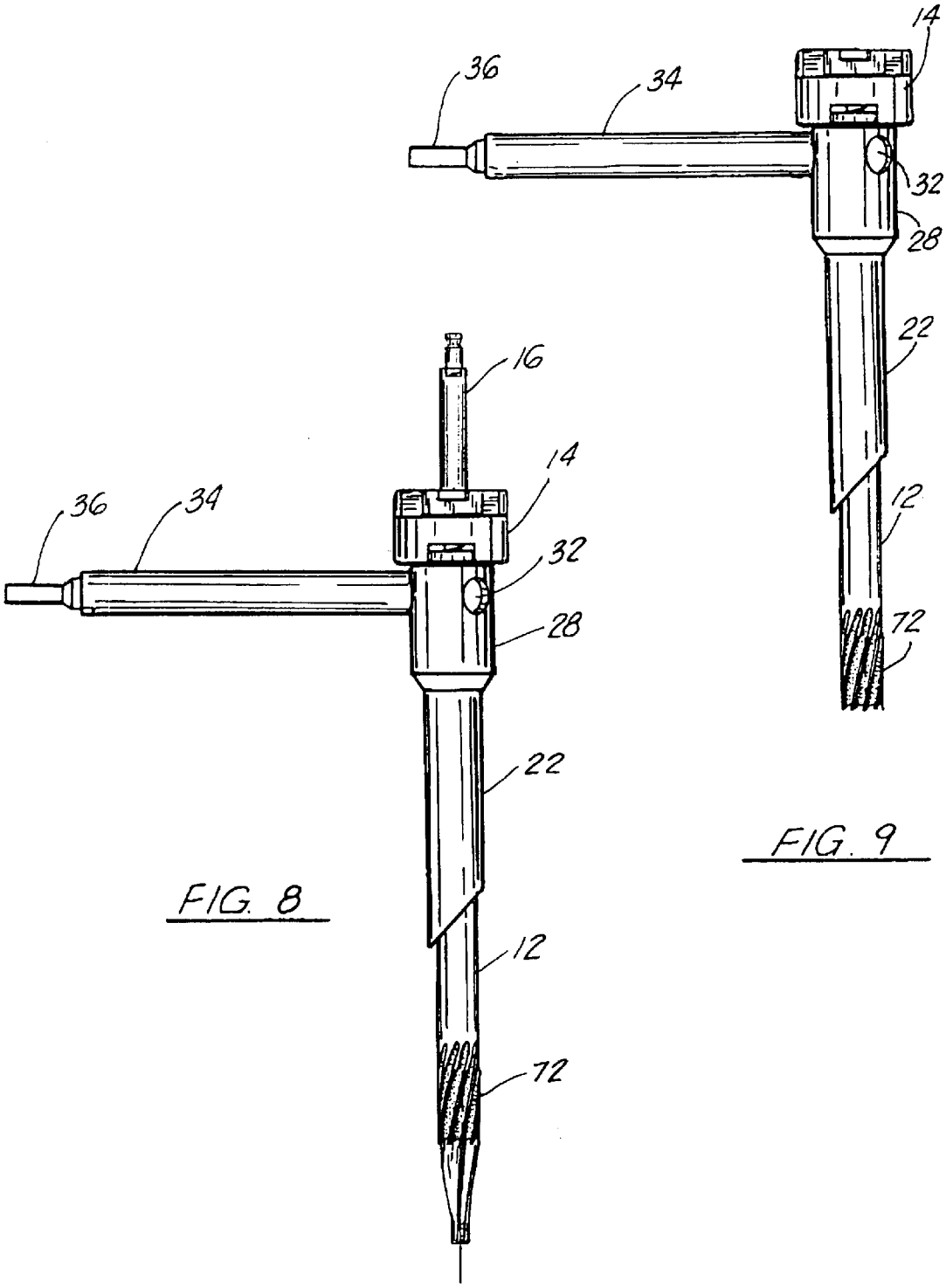
FIG. 8 is a side plan view of the present invention in combination with the entry portal tool.
FIG. 9 is a side plan view of the invention of FIG. 8 with the inner reamer removed.
Figure 11:
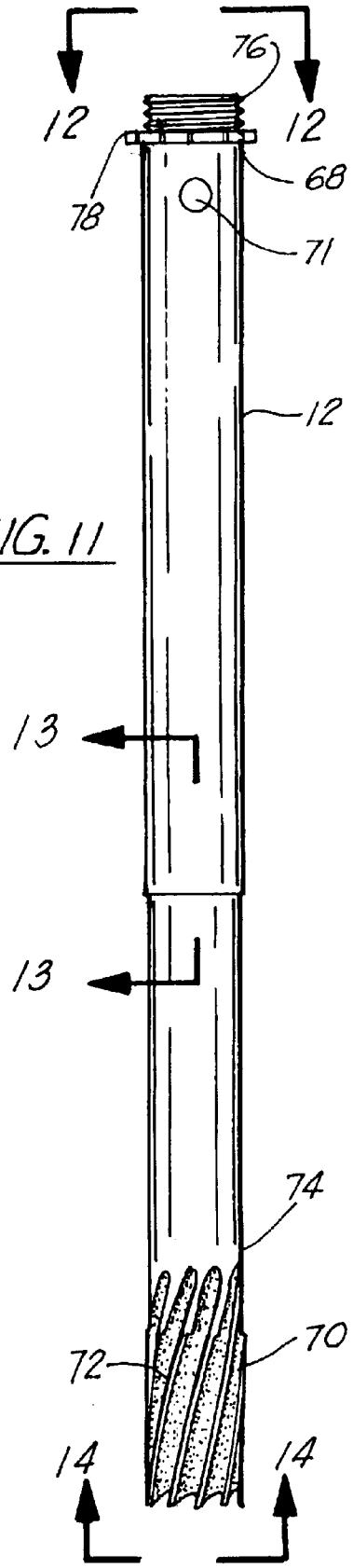
FIG. 11 is a side plan view of the reaming sleeve of the present invention.
Figure 12:
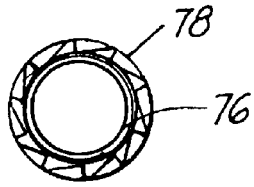
FIG. 12 is a plan view of the proximal end of the reaming sleeve of FIG. 11 taken along lines 12—12 of FIG. 11.
Figure 13:
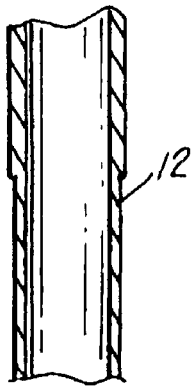
FIG. 13 is a partial cross-sectional view of the reaming sleeve of FIG. 11 taken along lines 13—13 of FIG. 11.
Figure 14:
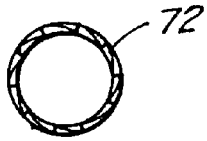
FIG. 14 is a plan view of the distal end of the reaming sleeve of FIG. 11 taken along lines 14—14 of FIG. 11.

In a preferred embodiment of the invention, the reaming assembly 10 and the entry portal tool 20 are used in combination to ream in a minimally invasive manner an intramedullary canal (FIGS. 1 and 8). Preferably, a surgeon first uses the entry portal tool 20 to locate the most desirable location for the entry portal in the proximal femur or other long or flat bones. The multiple openings 58 and 64 (*FIGS. 2–4*) of the conical tip and hubs 62, 66 of the entry portal tool 20 enable precise placement of the guide pin. This is especially important in repairing fractures of the femoral neck where very precise placement of the entry portal is required.

The surgeon makes an appropriate minimally invasive incision in the patient and using the entry portal tool handle 34, he or she inserts the entry portal sheath 22, with the obturator 50 inserted in the sheath 22, into the incision. The surgeon then places one or more guide pins (not shown) through a selected one of the plurality of openings 58, 64 in the obturator 50, and using fluoroscopy, evaluates the position of the guide pins. If the surgeon desires to change the position of the guide pins, he or she can place one or more of the pins into another opening, or can rotate the obturator 50 within the sheath 22 of the entry portal tool 20. Once the surgeon has selected the best position for the entry portal, he will insert the guide pin into the bone. With the pin firmly imbedded in the bone, the obturator 50 is removed from the sheath 22 of the entry portal tool 20.

The surgeon next inserts the reaming sleeve assembly 10 into sheath 22 and over the guide pin that is firmly imbedded in the bone (FIG. 8). The pin will act as a guide as the reamer assembly 10 reams an entry portal into the canal of the bone (FIG. 9). With the entry portal tool 20 and reamer assembly 10 still in place, the surgeon removes the inner reamer 16 from the assembly 10 by depressing the release button 122 on the housing 14. The one or more guide pins are also removed with the inner reamer 16, however, the reaming sleeve 12 remains in place in the canal of the bone. At this point, the reaming sleeve 12 becomes a working channel through which the intramedullary canal can be opened up to the appropriate diameter using progressively larger sized reamers as described above. A suction device attached to handle 34, 34A-B of the entry portal tool 20, 20A-B allows for the blood produced from the reaming to be suctioned up through holes 71 in the sleeve 12, into the sheath 22 of the entry portal tool 20, 20A-B and out its handle 34, 34A-B in to a collection container. Upon completion of the canal preparation, entry portal tool 20 and the reaming sleeve 12 are removed and an intramedullary nail (pin or rod) is inserted into the canal.

Thus, with the minimally invasive reaming assembly 10 of the present invention, an entry portal into the canal of a bone can be created by a surgeon, who then uses the same assembly to provide a working channel in which to progressively ream the canal of the bone without damaging the soft tissues or losing the entry portal into the bone.

Although the present invention has been described with reference to its preferred embodiments, those skilled in the art will recognize changes that may be made in form and structure that do not depart from the spirit of the invention already described in the specification and embodied in the claims that follow.

What is claimed is:

1. A minimally invasive reaming assembly for creating an entry portal into the canal of a bone and providing a working channel in which to ream the canal of a bone, the assembly comprising:

a) an elongated cylindrically-shaped hollow sleeve having a proximal and a distal end, the distal end having a plurality of cutting blades;

b) a housing adjacent to the proximal end of the sleeve, the housing having a top portion, a bottom portion and a through bore, the top portion including a first connecting [merhanism] *mechanism* configured to [releasebly] *releasably* engage an inner reamer, c) an inner reamer having an elongated body and proximal and distal ends, the distal end having a rotatable reaming head and the proximal end having a first mechanism configured to connect to a drill, a portion of the body including a second mechanism configured to engage with the housing, the reamer being sized and shaped for insertion through the bore of the housing and the sleeve;

d) whereas the minimally invasive reaming assembly is configured to create an entry portal into the canal of a bone and to provide a working channel in which a plurality of reamers of graduated sizes are inserted for progressively reaming the canal of a bone.

2. The assembly of claim 1, wherein the housing and sleeve are separate elements in which the bottom portion of the housing includes a second connecting mechanism configured to enrage with a sleeve connecting mechanism on the proximal end of the sleeve for releaseable attachment of the housing to the sleeve.

3. The assembly of claim 2, wherein the sleeve connecting mechanism of the proximal end of the sleeve includes threading for engaging with a threaded portion on a surface of the housing bore and a ring of horizontally placed teeth positioned below the threading on the sleeve.

4. The assembly of claim 3, wherein the second connecting mechanism of the bottom portion of the housing further includes a spring loaded lock for [releaseably] *releasably* engaging the horizontally placed teeth on the sleeve after the sleeve has been threaded into the housing.

5. The assembly of claim 1, wherein the first connecting mechanism of the top portion of the housing includes a notch sized and shaped for mating with a tab placed on the inner reamer.

6. The assembly of claim 5, wherein the first connecting mechanism of the top portion of the housing further includes a spring loaded release for releasing the tab on from the notch of the housing in order to remove the inner reamer from the housing and the sleeve.

7. The assembly of claim 1, wherein the inner reamer elongated body is cannulated.

8. The assembly of claim 1, used in combination with a positioning apparatus configured to locate an entry portal in a patient's bone, the apparatus comprising:

a) an elongated cylindrically-shaped hollow sheath having a proximal end, a distal end, and an upper and lower portion, the upper portion including at least one generally circular opening in the sheath;

b) an elongated handle having a proximal and distal end, the distal end including a mechanism configured to connect and disconnect the handle to the sheath, c) an elongated cylindrically-shaped tube having a proximal and distal end, the distal end having a tip with a plurality of openings, the tube having a central longitudinal axis;

d) the elongated tube including a plurality of openings at its proximal end, the plurality of openings of the proximal end and the tip being aligned along parallel lines that are parallel with the central longitudinal axis of the tube;

e) the elongated tube being sized and shaped for removable insertion into the hollow sheath and the hollow sheath being sized and shaped for removable insertion of the assembly of claim I into the hollow sheath;

f) wherein the combination of the assembly of claim 1 and the positioning apparatus allows for the correct placement of an entry portal into a patient's bone, the cutting of the entry portal into the bone canal and the reaming of the canal through the sleeve.

9. The assembly of claim 8, wherein the housing and sleeve are separate elements in which the bottom portion of the housing includes a second connecting mechanism configured to engage with a sleeve connecting mechanism of the proximal end of the sleeve for releaseable attachment of the housing to the sleeve.

10. The assembly of claim 9, wherein the sleeve connecting mechanism of the proximal end of the sleeve includes threading for engaging with a threaded portion on a surface of the housing bore and a ring of horizontally placed teeth positioned below the threading on the sleeve.

11. The assembly of claim 10, wherein the second connecting mechanism of the bottom portion of the housing further includes a spring loaded lock for [releaseably] *releasably* engaging the horizontally placed teeth on the sleeve after the sleeve has been threaded into the housing.

12. The assembly of claim 8, wherein the first connecting mechanism of the top portion of the housing includes a notch sized and shaped for mating with a tab of the inner reamer.

13. The assembly of claim 12, wherein the first connecting mechanism of the top portion of the housing further includes a spring loaded release for releasing the tab from the notch of the housing in order to remove the inner reamer from the housing and the sleeve.

14. The assembly of claim 8, wherein the sheath includes a plurality of generally circular openings.

15. The assembly of claim 8, wherein the elongated handle is configured to allow for the suction of fluids from the remaining site up through the sleeve and out the handle.

16. A minimally invasive method of creating an entry portal into the canal of a bone and providing a working channel in which to ream the canal of the bone, the method comprising the steps of:

a) locating an entry portal in a bone of a patient;

b) inserting a selected guide pin in the bone at the site of the entry portal;

c) creating a minimally invasive entry portal in the bone with a reaming assembly, with the guide pin acting as a guide for the assembly, the reaming assembly comprising:

i) an elongated cylindrically-shaped hollow sleeve having a proximal and a distal end, the distal end having a plurality of cutting blades;

ii) a housing adjacent to the sleeve, the housing having a top portion, a bottom portion and a through bore, the top portion including a first connecting mechanism configured to releasably engage an inner reamer;

iii) an inner reamer having an elongated cannulated body and proximal and distal ends, the distal end having a rotatable reaming head and the proximal end having a first mechanism configured to connect to a drill, a portion of the body including a second mechanism configured to is engage with the housing, the reamer being sized and shaped for insertion through the bore of the housing and the sleeve;

d) removing the guide pin and the inner reamer from the assembly while leaving the assembly in the entry portal in the bone;

e) inserting selected progressively larger sized reamers through the assembly to ream the canal of the bone to a larger diameter;

f) removing the assembly from the bone upon completion of the canal preparation; and g) inserting an intramedullary nail into the prepared canal.

17. The method of claim 16, including the steps of:

a) locating the entry portal of the bone with an entry portal tool, the tool comprising:

i) an elongated cylindrically-shaped hollow sheath having a proximal end, a distal end, and an upper and lower portion, the upper portion including at least one generally circular opening in the sheath;

ii) an elongated handle having a proximal and distal end the distal end including a mechanism configured to connect and disconnect) the handle to the sheath;

iii) an elongated cylindrically-shaped tube having a proximal and distal end, the distal end having a tip with a plurality of openings, the tube having a central longitudinal axis;

iv) the elongated tube including a plurality of openings at its proximal end, the plurality of openings of the proximal end and the tip being aligned along parallel lines that are parallel with the central longitudinal axis of the tube; and v) the elongated tube being sized and shaped for removable insertion into the hollow sheath and the hollow sheath being sized and shaped for removable insertion of [the] *a reaming* assembly [of claim 15] into the hollow sheath;

b) removing the elongated tube from the sheath; and c) inserting the reaming assembly into the sheath and over the guide pin inserted into the bone.

18. The method of claim 17, further including the steps of:

a) making an appropriate incision in a patient;

b) inserting the entry portal tool into the incision;

c) placing at least one guide pin through a selected one of the plurality of openings in the elongated tube;

d) evaluating the position of the guide pin; and e) inserting the at least one guide pin into the bone.

19. The method of claim 16 [and] *or* 17, [farther] *further* including the step of applying suction to the handle of the entry portal tool in order to suction fluids from a reaming site up through the sleeve and out through the handle.

20. A minimally invasive reaming assembly for creating an entry portal into the canal of a bone and providing a working channel in which to ream the canal of a bone, the assembly comprising:

a) an elongated cylindrically-shaped hollow sleeve having a proximal and a distal end, the distal end having a plurality of cutting blades;

b) a connecting mechanism on the proximal end of the sleeve configured to engage with an inner reamer;

c) an inner reamer having an elongated body and proximal and distal ends, the distal end having a rotatable reaming head and the proximal end having a first mechanism configured to connect to a drill, a portion of the body including a second mechanism configured to engage with the proximal end of the sleeve, the reamer being sized and shaped for insertion through a bore of a housing adjacent to and in communication with the hollow sleeve;

d) whereas the minimally invasive reaming assembly is configured to create an entry portal into the canal of a bone and to provide a working channel in which a plurality of reamers of graduated sizes are inserted for progressively reaming the canal of a bone.

*21. An assembly for providing an entry portal into the canal of a bone and a working channel for use in an intramedullary canal of a bone, comprising:*

*(a) an elongated cylindrically shaped hollow sleeve having a proximal and a distal end, the distal end having a plurality of cutting blades;*

*(b) a housing adjacent to the proximal end of the sleeve, the housing having a top portion, a bottom portion and a through bore, the top portion including a first connecting mechanism configured to releasably engage a reamer; and*

*(c) a reamer having an elongated body and proximal and distal ends, the distal end having a rotatable reaming head and the proximal end having a first mechanism configured to connect to a drill, a portion of the body including a second mechanism configured to engage with the housing, the reamer being sized and shaped for insertion through the bore of the housing and the sleeve.*

*22. An assembly for providing an entry portal into the canal of a bone and a working channel for use in an intramedullary canal of a bone, comprising:*

*(a) an elongated cylindrically shaped hollow sleeve having a proximal and a distal end;*

*(b) a housing adjacent to the proximal end of the sleeve, the housing having a top portion, a bottom portion and a through bore, the top portion including a first connecting mechanism configured to releasably engage a reamer;*

*(c) a reamer having an elongated body and proximal and distal ends, the distal end having a rotatable reaming head and the proximal end having a first mechanism configured to connect to a drill, a portion of the body including a second mechanism configured to engage with the housing, the reamer being sized and shaped for insertion through the bore of the housing and the sleeve;*

*(d) wherein the reaming assembly is configured to create an entry portal into the canal of a bone and to provide a working channel in which at least one object may be inserted for preparing the canal for placement of an intramedullary nail into a canal of a bone.*

*23. The assembly of claim 22 wherein the object is a reduction device.*

*24. The assembly of claim 22 wherein the object is a guide rod.*

*25. The assembly of claim 22 wherein the object is a reamer.*

*26. An assembly for providing an entry portal into the canal of a bone and a working channel for use in an intramedullary canal of a bone, comprising:*

*(a) an elongated cylindrically shaped hollow sleeve having a proximal and a distal end, the distal end having a plurality of cutting blades;*

*(b) a housing adjacent to the proximal end of the sleeve, the housing having a top portion, a bottom portion and a through bore, the top portion including a first connecting mechanism configured to releasably engage a reamer;*

*(c) a reamer having an elongated body and proximal and distal ends, the distal end having a rotatable reaming head and the proximal end having a first mechanism configured to connect to a drill, a portion of the body including a second mechanism configured to engage with the housing, the reamer being sized and shaped for insertion through the bore of the housing and the sleeve;*

*(d) wherein the reaming assembly is configured to create an entry portal into the canal of a bone and to provide a working channel in which at least one object may be inserted for preparing the canal for placement of an intramedullary nail into a canal of a bone.*

*27. The assembly of claim 26 wherein the object is a reduction device.*

*28. The assembly of claim 26 wherein the object is a guide rod.*

*29. The assembly of claim 26 wherein the object is a reamer.*

*30. An assembly for providing an entry portal into the canal of a bone and a working channel for use in an intramedullary canal of a bone, comprising:*

*(a) an elongated cylindrically shaped hollow sleeve having a proximal and a distal end;*

*(b) a reamer having an elongated body and proximal and distal ends, the distal end having a rotatable reaming*

*head and the proximal end having a first mechanism configured to connect to a drill, the reamer being sized and shaped for insertion through the bore of the housing and the sleeve;*

(*c*) *wherein the reamer is adapted to be disposed within the sleeve and is adapted to be engaged with the sleeve in a manner that causes the sleeve to rotate when the reamer rotates; and*

(*d*) *wherein the reaming assembly is configured to create an entry portal into the canal of a bone and to provide a working channel in which at least one object may be inserted for preparing the canal for placement of an intramedullary nail into a canal of a bone.*

*31. The assembly of claim 30 wherein the object is a reduction device.*

*32. The assembly of claim 30 wherein the object is a guide rod.*

*33. The assembly of claim 30 wherein the object is a reamer.*

*34. The assembly of claim 30 wherein the reamer is adapted to be engaged with the sleeve in a releasing fashion.*

*35. An assembly for providing an entry portal into the canal of a bone and a working channel for use in an intramedullary canal of a bone, comprising:*

(*a*) *an elongated cylindrically shaped hollow sleeve having a proximal and a distal end, the distal end having a plurality of cutting blades;*

(*b*) *a reamer having an elongated body and proximal and distal ends, the distal end having a rotatable reaming head and the proximal end having a first mechanism configured to connect to a drill, the reamer being sized and shaped for insertion through the bore of the housing and the sleeve;*

(*c*) *wherein the reamer is adapted to be disposed within the sleeve and is adapted to be engaged with the sleeve in a manner that causes the sleeve to rotate when the reamer rotates; and*

(*d*) *wherein the reaming assembly is configured to create an entry portal into the canal of a bone and to provide a working channel in which at least one object may be inserted for preparing the canal for placement of an intramedullary nail into a canal of a bone.*

*36. The assembly of claim 35 wherein the object is a reduction device.*

*37. The assembly of claim 35 wherein the object is a guide rod.*

*38. The assembly of claim 35 wherein the object is a reamer.*

*39. The assembly of claim 35 wherein the reamer is adapted to be engaged with the sleeve in a releasing fashion.*

*40. A method for creating an entry portal into the canal of a bone and providing a working channel in the canal of the bone, comprising:*

(*a*) *inserting a selected guide pin in the bone at the site desired for an entry portal;*

(*b*) *reaming the bone by inserting a reamer over the guide pin, the pin acting as a guide for the reamer, the reamer comprising an elongated body and proximal and distal ends, the distal end having a rotatable reaming head and the proximal end having a first mechanism configured to connect to a drill;*

(*c*) *inserting an elongated cylindrically shaped hollow sleeve over the guide pin and reamer and into the entry portal in the bone;*

(*d*) *removing the guide pin and reamer;*

(*e*) *inserting at least one object for preparing the canal for placement of an intramedullary nail into a canal of a bone;*

(*f*) *removing the sleeve upon completion of the canal preparation; and*

(*g*) *inserting an intramedullary nail into the prepared canal.*

*41. The method of claim 40 wherein the inserting at least one object comprises inserting a reduction device.*

*42. The method of claim 40 wherein the inserting at least one object comprises inserting a guide rod.*

*43. The method of claim 40 wherein the inserting at least one object comprises inserting a reamer.*

*44. A method for creating an entry portal into the canal of a bone and providing a working channel in the canal of the bone, comprising:*

(*a*) *inserting a selected guide pin in the bone at the site desired for an entry portal;*

(*b*) *creating an entry portal in the bone with a reaming assembly, with the guide pin acting as a guide for the assembly, the reaming assembly comprising:*

(*i*) *an elongated cylindrically shaped hollow sleeve; and*

(*ii*) *a reamer having an elongated body and proximal and distal ends, the distal end having a rotatable reaming head and the proximal end having a first mechanism configured to connect to a drill, the reamer being sized and shaped for translation within the sleeve;*

*wherein at least part of the reaming assembly enters a canal of the bone;*

(*c*) *removing the guide pin and reamer from the assembly while leaving the sleeve in the entry portal in the bone;*

(*d*) *inserting at least one object for preparing the canal for placement of an intramedullary nail into a canal of a bone;*

(*e*) *removing the assembly from the bone upon completion of the canal preparation; and*

(*f*) *inserting an intramedullary nail into the prepared canal.*

*45. The method of claim 44 wherein the inserting at least one object comprises inserting a reduction device.*

*46. The method of claim 44 wherein the inserting at least one object comprises inserting a guide rod.*

*47. The method of claim 44 wherein the inserting at least one object comprises inserting a reamer.*

*48. A method for creating an entry portal into the canal of a bone and providing a working channel in the canal of the bone, comprising:*

(*a*) *inserting a selected guide pin in the bone at the site desired for an entry portal;*

(*b*) *reaming the bone by inserting an elongated cylindrically shaped hollow sleeve over the guide pin, the sleeve having a proximal and a distal end, the distal end having a plurality of cutting blades;*

(*c*) *removing the guide pin from the sleeve while leaving the sleeve in the entry portal in the bone;*

(*d*) *inserting at least one object for preparing the canal for placement of an intramedullary nail into a canal of a bone;*

(*e*) *removing the sleeve from the bone upon completion of the canal preparation; and*

(*f*) *inserting an intramedullary nail into the prepared canal.*

*49. The method of claim 48 wherein the inserting at least one device comprises inserting a reduction device.*

*50. The method of claim 48 wherein the inserting at least one object comprises inserting a guide rod.*

*51. The method of claim 48 wherein the inserting at least one object comprises inserting a reamer.*

* * * * *